United States Patent [19]

Daher

[11] Patent Number: 5,348,745
[45] Date of Patent: Sep. 20, 1994

[54] AQUEOUS GRANULATION SOLUTION AND A METHOD OF TABLET GRANULATION

[75] Inventor: Lawrence J. Daher, Elkhart, Ind.

[73] Assignee: Miles Inc., Elkhart, Ind.

[21] Appl. No.: 879,696

[22] Filed: May 5, 1992

Related U.S. Application Data

[63] Continuation of Ser. No. 639,908, Jan. 10, 1991, abandoned, which is a continuation-in-part of Ser. No. 349,060, May 9, 1989, abandoned.

[51] Int. Cl.$^5$ .......................... A61K 9/46; A61K 9/16
[52] U.S. Cl. .................................. 424/466; 424/484; 424/717; 514/819; 514/960; 514/970
[58] Field of Search ............... 424/466, 464, 465, 484, 424/717, 44; 514/819, 960, 970

[56] References Cited

U.S. PATENT DOCUMENTS

| | | | |
|---|---|---|---|
| Re. 33,086 | 10/1989 | Bru | 424/44 |
| 3,903,255 | 9/1975 | Gusman et al. | 424/44 |
| 4,004,036 | 1/1977 | Schmidt | 514/163 |
| 4,127,645 | 11/1978 | Witzel et al. | 424/44 |
| 4,664,915 | 5/1987 | Simonian | 424/44 |
| 4,687,662 | 8/1987 | Schobel | 424/44 |
| 4,689,218 | 8/1987 | Gazzaniga et al. | 424/43 |
| 4,704,269 | 11/1987 | Korab | 424/44 |
| 4,716,046 | 12/1987 | Lavie | 424/466 |
| 4,824,664 | 4/1989 | Tarral et al. | 424/446 |
| 4,867,942 | 9/1989 | Gergely et al. | 424/466 |

FOREIGN PATENT DOCUMENTS

| | | |
|---|---|---|
| 085376 | 10/1982 | Fed. Rep. of Germany . |
| 8402468 | 7/1984 | France . |
| 882567 | 11/1961 | United Kingdom . |
| 1475861 | 6/1977 | United Kingdom . |

*Primary Examiner*—Edward J. Webman
*Attorney, Agent, or Firm*—Mary G. Boguslaski

[57] ABSTRACT

The invention discloses an aqueous granulating solution containing sodium, potassium or mixed sodium potassium salt of an edible organic acid selected from the group consisting of citric, malic, tartaric and fumaric acid and optionally containing sodium or potassium bicarbonate. The granulating solution is especially useful for granulating finely divided solids including acetaminophen, ketoprofen or calcium carbonate. The resulting granulate may be used to prepare a swallow tablet or mixed with an edible organic acid and the mixture tableted to provide an effervescent tablet without resorting to controlled reaction or special handling techniques.

4 Claims, No Drawings

AQUEOUS GRANULATION SOLUTION AND A METHOD OF TABLET GRANULATION

This is a continuation of application Ser. No. 639,908, filed Jan. 10, 1991, now abandoned, which is a continuation-in-part of U.S. Ser. No. 349,060 filed May 9, 1989, now abandoned.

FIELD OF THE INVENTION

The invention relates to the use of aqueous solutions of alkali metal salts of edible organic acids as granulating agents, granulates of finely divided solids made using such solutions and a method of wet granulation using these granulating solutions. The granulating solutions and method are useful for the production of pharmaceutical tablets and granulations, particularly effervescent tablets.

BACKGROUND OF THE INVENTION

Wet granulation techniques have been used for many years by the pharmaceutical industry. Traditional granulating agents such as starch, gelatin, sucrose, acacia, hydroxypropylmethylcellulose and polyvinylpyrrolidone have been used to provide a freely flowing granulation mixture, tabletability, aqueous solubility or dispersibility of the medically effective ingredient, and so forth. Alkali metal salts of edible organic acids such as trisodium citrate, tripotassium citrate, dipotassium fumarate and sodium potassium tartrate have not been used in aqueous solutions as granulating agents previously. Trisodium citrate has been used in powder form as a stabilizer for dichloraphenazone (GB 882567) which mixture is then granulated to form tablets for pharmaceutical use.

Gusman et al disclose the use of granulating powder mixtures (which may contain potassium citrate and potassium bicarbonate) with alcoholic solutions of polymeric binding agents such as polyvinylpyrrolidone and polyethylene glycol.

Special problems have been found with the granulation and tableting of effervescent compositions because the compounds required for the effervescent couple react during granulation. Methods have been developed which involve the controlled reaction of the effervescent couple to produce a dry granulation mixture of the couple. This mixture must be carefully handled in a humidity controlled environment. The medically effective ingredient, often an analgesic, is granulated separately and the two granulation mixtures combined for tableting. A commonly used reactant in effervescent mixtures, sodium bicarbonate, is not wet granulated as such or in mixtures in the preparation of stable effervescent systems, except in carefully controlled reaction systems containing the acidic components of the effervescent couple and using very small amounts of water or water-solvent mixtures. Even then, the granulation is sometimes aided by heat to liberate water from the sodium bicarbonate by decomposition. Sodium citrate may be formed as the reaction product between the components of effervescent couples such as sodium bicarbonate and citric acid when granulated together. However, special precautions, by drying or controlling the reaction, have been required.

It has now been found that by using an aqueous solution containing an effective amount of an alkali metal salt of an edible organic acid as a granulating agent, traditional wet granulating techniques may be used. These granulating agents allow all of the nonacid components of the desired final formulation to be granulated together without special handling techniques.

SUMMARY OF THE INVENTION

The invention discloses a method of preparing a granulate of a finely divided solid material, by mixing a finely divided solid material requiring granulation with an aqueous granulating solution comprising potassium or sodium or mixed sodium potassium salt of an edible organic acid selected from the group consisting of citric acid, malic acid, fumaric acid and tartaric acid, which granulating solution is added in an amount effective to prepare a moist mass; granulating the moist mixture and drying the granulated mixture. The granulating solution may also contain sodium or potassium bicarbonate.

Medically effective ingredients such as acetaminophen, calcium carbonate, ketoprofen or sodium or potassium bicarbonate may be granulated by this method, as well as many others which are not acidic or minimally acidic. The dried granulate may then mixed with an edible organic acid to form an effervescent powder which may be tableted into conventional effervescent tablets; or, as appropriate, the dried granulate may be mixed with other tableting excipients and made into swallow tablets.

DESCRIPTION OF THE INVENTION

It has been found that aqueous solutions of potassium or sodium or mixed sodium potassium salt of an edible organic acid chosen from the group consisting of citric acid, malic acid, fumaric acid and tartaric acid may be used as granulating agents. Trisodium citrate, tripotassium citrate, dipotassium fumarate and sodium potassium tartrate are particularly preferred for use with bicarbonates and nonacid ingredients which will be tableted with reactive ingredients such as organic acids.

Usage of this wet granulation method with trisodium citrate has allowed for the successful large scale manufacturing of effervescent tablets containing, among other things, potassium bicarbonate and fumaric acid. Severe production problems, based on the spontaneous reaction of potassium bicarbonate and fumaric acid were found when these ingredients were simply dry mixed together. Use of an aqueous granulated form of potassium bicarbonate protected with a granulating agent of this invention eliminated this problem.

As used herein, the phrase "aqueous granulating solution" refers to a solution of the alkali metal salt of an edible organic acid such as the potassium, sodium or mixed sodium potassium salts mentioned previously. The aqueous granulating solutions may optionally contain sodium or potassium bicarbonate. The term "granulate" refers to the dried mixture granulated with the addition of the aqueous granulating solution. To form a final formulation or tablet, the granulate may be mixed with other ingredients or used as is.

As used herein, the phrase "an effective amount" refers to the amount of granulating solution required to produce a moistened mass upon mixing, such that the component powder ingredient particles bind together to form larger particles or aggregates rather than remaining as their individual starting particle sizes, without overwetting the powder mass so that a paste or fluid is formed. This amount is dependent upon the variables of the whole granulation system, including the equipment used, the batch size, the nature and composition of the powders being granulated, the nature and composition of the granulating solution, the mixing time, the intended subsequent method of granule sizing operation and the equipment to be used for that operation and the matching of the final granulate to the needs of its intended use in pharmaceutical compositions. The amounts used in the examples provide a guide for those of skill in the art, who will be able determine the amount required with other compositions and equipment.

An aqueous granulating solution of trisodium citrate or of trisodium citrate and potassium bicarbonate is especially useful for granulating mixtures of metallic salts of bicarbonate and carbonate and other formula ingredients for multicomponent effervescent mixtures. The trisodium citrate granulate mixture incorporating a bicarbonate is mixed and tableted with an edible organic acid such as citric, malic, fumaric acid, and the like, to produce an effervescent tablet. Such mixtures then show high dissolution reactivity rates as well as good binding characteristics for tableting, good free flowing properties, good dispersal properties for contained insoluble particles such as aspirin and acetaminophen and high reactivity rates for insoluble carbonates like calcium carbonate.

In effervescent formulations, a bicarbonate and an organic acid are used as the effervescent couple. Traditionally the bicarbonate has been either sodium or potassium bicarbonate and the organic acid has been citric acid. The organic acid may, however, also be fumaric, tartaric, malic or succinic acid or any one of a number of edible organic acids. When potassium bicarbonate and fumaric acid are used together, without prior protective treatment, the two ingredients react spontaneously, creating a problem in the traditional tableting procedures. In solving this problem, it was found that trisodium citrate, tripotassium citrate, dipotassium fumarate, and/or sodium potassium tartrate could be granulated onto potassium bicarbonate and any other nonacid components of the formulation in need of granulation by traditional wet granulation methods. The organic acid could then be mixed with the dried nonacid granulation and tableted. This means that it is no longer necessary to use controlled reaction methods of preparing the effervescent couple granulation. Production of effervescent tablets, or powders, is therefore substantially simplified. This simplification leads to increased convenience and decreased cost of manufacture.

The nonacid components which may be included in the trisodium citrate, tripotassium citrate, dipotassium fumarate, or sodium potassium tartrate wet granulation are varied, but it is particularly convenient to add pharmaceutically active ingredients which require granulation. Such ingredients include calcium carbonate and analgesics, especially acetaminophen, which is difficult to granulate. Although the granulate is primarily applicable to nonacid components, slightly acidic components can be tolerated, for example ketoprofen. The phrase "nonacid components" is generally intended to exclude the major acidic ingredient which would make up the acid component of the effervescent couple. These "nonacid" ingredients may be included alone or in combination with potassium and/or sodium bicarbonate. The formulation may of course be an antacid where potassium and/or sodium bicarbonate may be used as the pharmaceutically active ingredient. Other nonacid ingredients may also be included, such as flavors, bulking agents and the like.

The aqueous granulating solution is commonly a saturated solution of the alkali metal salt at ambient temperature to provide for ease of preparation and convenience. For example, for trisodium citrate this is about 40% weight/weight (w/w); for dipotassium fumarate, this is about 20% w/w; and for sodium potassium tartrate, this is about 40% w/w. When the sodium or potassium bicarbonate is added to the aqueous granulating solution the proportion may be, for example, trisodium citrate 20% w/w and potassium bicarbonate 10% w/w. The concentrations given herein are based on the use of water as a solvent. Variation of these concentrations is well within the skill of those versed in the art given the guidance found herein. Of course lower concentrations (i.e. a higher percentage of water in the granulating solution) would be possible if longer drying times or higher drying temperatures were considered acceptable. It is preferred that the pH of the aqueous granulating solution be about neutral, or about pH 7 or above, especially when the granulate contains a bicarbonate and will be used to prepare an effervescent couple, in order to avoid reaction with the bicarbonate. Therefore, essentially neutralized salts, such as trisodium citrate, tripotassium citrate, dipotassium fumarate and sodium potassium tartrate are preferred.

The following examples disclose preferred embodiments of the invention, but do not limit the applicability of the invention which is solely defined by the claims.

EXAMPLES

In the following examples, the granulating solution refers to an aqueous solution containing sodium, potassium or mixed sodium potassium salt or an edible organic acid such as citric, malic, tartaric or fumaric acid and optionally sodium or potassium bicarbonate. Sodium citrate is used as a synonym for trisodium citrate. The formulas shown for the granulate include the concentration of alkali metal salt, and optionally bicarbonate, contributed by the aqueous granulating solution and remaining in the mixture when the granulate is dried. The general procedure is to load the finely divided solid material requiring granulation together into a Patterson-Kelley V-Blender, with an intensifier bar. The blender used for experimental purposes had a capacity of eight quarts. The blender is then run, with the intensifier bar on, while the granulating solution is added; and the run is continued for an additional time of about four minutes. The amount of time the blender is run is approximate and can readily be determined by one of ordinary skill in the art for various formulations. The granulate is then discharged from the blender and spread onto a tray to dry overnight, or about 16 hours, in a forced hot air oven at 60° C. The time, temperature or equipment used in drying is not critical as long as it is sufficient to dry the granulate without causing decomposition of the components. For example, a fluid bed dryer may be used in place of a forced air oven. The general procedure outlined above is used in the examples unless otherwise specified.

EXAMPLE 1—Preparation of a Trisodium Citrate Granulate of Potassium Bicarbonate, G-6.

A granulate of potassium bicarbonate was prepared using an aqueous solution of trisodium citrate as the granulating agent. This granulate may be mixed with other formula ingredients, including fumaric acid, and tableted without special handling techniques to produce an effervescent antacid tablet. When potassium bicarbonate is not so protected during granulation, the bicarbonate will react spontaneously with fumaric acid.

| % w/w | Ingredient | Wt. |
|---|---|---|
| | Granulating Solution | |
| 40.0 | Sodium Citrate, Dihydrate | 8.0 kg |
| 60.0 | D. I.* Water | 12.0 kg |
| 100.0 | | 20.0 kg |
| | Granulate, G-6 | |
| 95.8 | Potassium Bicarbonate, U.S.P. | 136 kg |
| 4.2 | Sodium Citrate | 6 kg |
| 100.0 | | 142 kg |

*D. I. is an abbreviation for "deionized"

The granulating solution is prepared by dissolving the sodium citrate in the D.I. Water with stirring. The granulate, G-6, is prepared in a Littleford-Lodige Mixer/Granulator of nine cubic foot total capacity. Potassium bicarbonate (300 lbs.) is loaded into the mixer. The mixer is run for three minutes with the choppers turned on, in order to break up any lumps in the material. A total of 15.0 kg of granulating solution is added to the mixer while it is running, with the choppers on. The mixer is run for eleven minutes, until a suitable granulate is formed. The granulate is discharged from the mixer and dried at 82° C.

The comparative dry state reactivity of micronized fumaric acid with potassium bicarbonate versus its reactivity with G-6 was studied by mixing 10 Gm of each and placing in a closed container with a moisture trap in the vent. The container was held at room temperature (24° C.) and weighed at selected intervals. When dried but untreated potassium bicarbonate was used, there was a weight loss due to evolution of carbon dioxide, which proceeded rapidly at a rate of about 2 Gm/hour, to near 70% completion, at which time there was an abrupt change to a rate of about 0.002 Gm/hour. When G-6 granulate of Example 1 was used in place of dried, but untreated, potassium bicarbonate, there was no perceptible reaction over 143 hours.

EXAMPLE 2—Preparation of a Trisodium Citrate and Potassium Bicarbonate Granulate of Sodium Bicarbonate, G-80.

A granulate of sodium bicarbonate was prepared using an aqueous solution of trisodium citrate and potassium bicarbonate as the granulating agent. This granulate was useful for the preparation of effervescent aspirin tablets.

| % w/w | Ingredient | Wt. |
|---|---|---|
| | Granulating Solution | |
| 20.0 | Sodium Citrate Dihydrate | 400 Gm |
| 10.0 | Potassium Bicarbonate, U.S.P. | 200 Gm |
| 70.0 | D.I. Water | 1400 Gm |
| 100.0 | | 2000 Gm |
| | Granulate, G-80 | |
| 97.9 | Sodium Bicarbonate, U.S.P.* | 7000 Gm |
| 1.4 | Sodium Citrate | 100 Gm |
| 0.7 | Potassium Bicarbonate | 50 Gm |
| 100.0 | | 7150 Gm |

*Church and Dwight Co., Inc.; #2 Fine Granular

The granulating solution is prepared by dissolving the sodium citrate and the potassium bicarbonate in the D.I. Water with stirring. The granulate, G-80, is prepared as described in the general procedure above. The sodium bicarbonate is loaded into the blender. A total of 500 Gm of granulating solution is added to the blender. The blender is run for an additional four minutes after the granulating solution has been added. The resulting granulate is discharged from the mixer and dried.

The granulate, G-80, composed primarily of bicarbonate was used to prepare an effervescent analgesic preparation containing aspirin.

| | Formula ET-179 | |
|---|---|---|
| mg/tab | Ingredient | Wt. |
| 325 | Aspirin, U.S.P. | 162.5 Gm |
| 1000 | Citric Acid, Anhydrous Powder | 500.0 Gm |
| 1957 | G-80 | 978.5 Gm |
| 3282 | | 1641.0 Gm |

The G-80 granulate was dry sized by passage through a 2B S.S. drilled screen on a Model M Fitzpatrick Comminuting Mill, operating at 2500 rpm, knives forward. Together the citric acid and aspirin are passed through a #24 S.S. Screen, U.S. Standard. This mixture and the G-80 granulate are loaded into a tabletop Patterson-Kelley Twin Shell Blender, and mixed for eight minutes. The final mixture is compressed into tablets of one inch diameter to a tablet hardness of 9–12 kilopounds (kp).

The resulting tablets dissolve rapidly (within approximately one minute) when placed in water. The dissolved tablet solution has good esthetic properties; the aspirin crystals on the surface are easily dispersed into the solution by swirling, without leaving an unsightly scum ring on the sides of the glass, and the solution has a prolonged residual effervescence.

EXAMPLE 3—Preparation of a Trisodium Citrate Granulate of a Mixture of Potassium Bicarbonate and Acetaminophen.

An aqueous granulating solution of trisodium citrate was used to produce a granulate composed of potassium bicarbonate and acetaminophen.

| % w/w | Ingredient | Wt. |
|---|---|---|
| | Granulating Solution | |
| 40.0 | Sodium Citrate, Dihydrate | 8.0 kg |
| 60.0 | D.I. Water | 12.0 kg |
| 100.0 | | 20.0 kg |
| | Granulate, G-73 | |
| 45.6 | Potassium Bicarbonate, U.S.P. | 2100.0 Gm |
| 49.5 | Acetaminophen, U.S.P. | 2275.0 Gm |
| 4.9 | Sodium Citrate | 224.5 Gm |
| 100.0 | | 4599.5 Gm |

The granulate is prepared as described in the general procedure. Potassium bicarbonate and acetaminophen are loaded into the blender and are dry mixed for four minutes. A total of 600 Gm of granulating solution is added to the blender while it is running. The blender is then run for a total of 15 minutes. The granulate is discharged from the mixer and dried at 71° C.

EXAMPLE 4—Preparation of a Trisodium Citrate Granulate of a Mixture of Potassium Bicarbonate Acetaminophen and Calcium Carbonate.

Acetaminophen and calcium carbonate are both finely divided solids which are difficult to granulate and tablet. It was found that an aqueous solution of trisodium citrate could be successfully used to prepare a granulate containing these ingredients and potassium bicarbonate. This granulate may be used to prepare an effervescent tablet without special handling techniques.

| % w/w | Ingredient | Wt. |
|---|---|---|
| | Granulating Solution | |
| 40.0 | Sodium Citrate, Dihydrate | 8.0 kg |
| 60.0 | D.I. Water | 12.0 kg |
| 100.0 | | 20.0 kg |
| | Granulate, G-74 | |
| 28.6 | Precipitated Calcium Carbonate, U.S.P. | 1255.5 Gm |
| 30.8 | Potassium Bicarbonate, U.S.P. | 1350.0 Gm |
| 33.3 | Acetaminophen, U.S.P. | 1462.5 Gm |
| 7.3 | Sodium Citrate | 320.0 Gm |
| 100.0 | | 4388.0 Gm |

The granulate, G-74, is prepared as described in the general procedure. Calcium carbonate, potassium bicarbonate and acetaminophen are loaded into the blender and are dry mixed for four minutes. A total of 800 Gm of granulating solution is added to the blender while it is running. The blender is run for four minutes after the solution has been added. The granulate is discharged from the mixer and dried at 71° C.

EXAMPLE 5—Preparation of a Trisodium Citrate Granulate of a Mixture of Sodium Bicarbonate, Calcium Carbonate, Potassium Bicarbonate and Acetaminophen.

In order to show that amount of solids which may be granulated may vary, as may the amount of bicarbonate, another granulate was prepared with an aqueous trisodium citrate granulating solution.

| % w/w | Ingredient | Wt. |
|---|---|---|
| | Granulating Solution | |
| 40.0 | Sodium Citrate, Dihydrate | 8.0 kg |
| 60.0 | D.I. Water | 12.0 kg |
| 100.0 | | 20.0 |
| | Granulate, G-76 | |
| 32.5 | Sodium Bicarbonate, U.S.P.* | 1662.5 Gm |
| 19.1 | Precipitated Calcium Carbonate USP | 976.5 Gm |
| 20.6 | Potassium Bicarbonate, U.S.P. | 1050.0 Gm |
| 22.3 | Acetaminophen, U.S.P. | 1137.5 Gm |
| 5.5 | Sodium Citrate | 280.0 Gm |
| 100.0 | | 5106.5 Gm |

*Church and Dwight Co., Inc.; #5 Coarse Granular

The granulate, G-76, is prepared as described in the general procedure. Sodium bicarbonate, calcium carbonate, potassium bicarbonate and acetaminophen are loaded into the blender and dry mixed for four minutes. A total of 700 Gm of granulating solution is added to the blender while it is running. The blender is run for five minutes after the solution has been added. The granulate is discharged from the mixer and dried.

The granulate, G-76, containing acetaminophen is used to prepare an effervescent analgesic tablet.

| | Formula ET-185 | |
|---|---|---|
| mg/tab | Ingredient | Wt. |
| 1459 | G-76 | 437.7 Gm |
| 887 | Citric Acid, Anhydrous Powder | 266.1 Gm |
| 553 | DiPac ®, Sugar | 165.9 Gm |
| 80 | Fumaric Acid, Micronized | 24.0 Gm |
| 1 | Polyvinylpyrrolidone, K29-32 | 0.3 Gm |
| 2980 | | 894.0 Gm |

The G-76 granulate was dry sized by passage through a 0.033 inch opening, drilled S.S. screen at 3550 rpm, on a Model JT Homoloid Machine of the W. J. Fitzpatrick Co. Citric acid, DiPac sugar and fumaric acid were passed through a #16 S.S. Screen, U.S. Standard. This mixture, the G-76 granulate and the polyvinylpyrrolidone are loaded into a jar, closed with a lid, and mixed for seven minutes on a Turbula Type T10B Mixer. The final mixture is compressed into tablets of one inch diameter to a tablet hardness of 6–8 Kp.

The resulting tablets dissolve rapidly (within approximately one minute and 20 seconds) when placed in water. The dissolved tablet solution has good esthetic properties; there is no surface scum of insoluble materials to deal with, the solution has only a slight turbidity to it (which clears upon standing), and the solution has a prolonged residual effervescence.

EXAMPLE 6—Preparation of a Trisodium Citrate Granulate of Acetaminophen.

An aqueous solution of trisodium citrate may be used as a granulating agent without the addition of a bicarbonate.

| % w/w | Ingredient | Wt. |
|---|---|---|
| | Granulating Solution | |
| 40.0 | Sodium Citrate, Dihydrate | 8.0 kg |
| 60.0 | D.I. Water | 12.0 kg |
| 100.0 | | 20.0 kg |
| | Granulate, G-77 | |
| 89.8 | Acetaminophen | 3500 Gm |
| 10.2 | Sodium Citrate | 400 Gm |
| 100.0 | | 3900 Gm |

The granulate, G-77, is prepared as described in the general procedure. Acetaminophen is loaded into the blender. A total of 1000 Gm of granulating solution is added to the blender while it is running. The blender is run for five minutes after the solution has been added. The granulate is discharged from the mixer and dried.

EXAMPLE 7—Preparation of a Trisodium Citrate Granulate of a Mixture of Ketoprofen, Sodium Bicarbonate, Calcium Carbonate and Potassium Bicarbonate.

An aqueous solution of trisodium citrate was successfully used to granulate a mixture composed of bicarbonates, calcium carbonate and a slightly acidic analgesic, ketoprofen. The resulting granulate may be used to prepare an effervescent sachet.

| % w/w | Ingredient | Wt. |
|---|---|---|
| | Granulating Solution | |
| 40.0 | Sodium Citrate, Dihydrate | 8.0 kg |
| 60.0 | D.I. Water | 12.0 kg |
| 100.0 | | 20.0 kg |
| | Granulate, G-78 | |
| 2.2 | Ketoprofen** | 112.5 Gm |
| 41.8 | Sodium Bicarbonate, U.S.P.* | 2137.5 Gm |
| 24.5 | Precipitated Calcium Carbonate, U.S.P. | 1255.5 Gm |

| % w/w | Ingredient | Wt. |
|---|---|---|
| | -continued | |
| 26.4 | Potassium Bicarbonate, U.S.P. | 1350.0 Gm |
| 5.1 | Sodium Citrate | 260.0 Gm |
| 100.0 | | 5115.5 Gm |

*Church and Dwight Co., Inc.; #5 Coarse Granular
**Ketoprofen is an acidic compound. However, the resultant granulate is not acidic.

The granulate, G-78, is prepared as described in the general procedure. Ketoprofen, sodium bicarbonate, calcium carbonate and potassium bicarbonate are loaded into the blender and are dry mixed for four minutes. A total of 650 Gm of granulating solution is added to the blender while it is running. The blender is run for six minutes after the solution has been added. The granulate is discharged from the mixer and dried.

This run indicates the ability of granulates to accommodate minor amounts of stable acidic ingredients.

G-78 contains 2.2% of ketoprofen, a proprionic acid derivative. Granulation of this small amount of an acidic drug within the bicarbonate-carbonate mixture is easily accomplished using trisodium citrate wet granulation methodology. G-78 granulate is useful for the formulation and preparation of sachet dosage forms of ketoprofen, without the fear of ketoprofen active ingredient segregation despite its low concentration within the bulk of the formulation dosage.

EXAMPLE 8—Preparation of a Trisodium Citrate and Potassium Bicarbonate Granulate of a Mixture of Potassium Bicarbonate, Calcium Carbonate and Sodium Bicarbonate.

An aqueous solution of trisodium citrate and potassium bicarbonate may be used to granulate bicarbonates and calcium carbonate.

| % w/w | Ingredient | Wt. |
|---|---|---|
| | Granulating Solution | |
| 20 | Sodium Citrate, Dihydrate | 240 Gm |
| 10 | Potassium Bicarbonate, U.S.P. | 120 Gm |
| 70 | D.I. Water | 840 Gm |
| 100 | | 1200 Gm |
| | Granulate, G-79 | |
| 33.0 | Potassium Bicarbonate, U.S.P. | 1560 Gm** |
| 26.4 | Precipitated Calcium Carbonate, U.S.P. | 1250 Gm |
| 38.1 | Sodium Bicarbonate, U.S.P.* | 1800 Gm |
| 2.5 | Sodium Citrate | 120 Gm |
| 100.0 | | 4730 Gm |

*Church and Dwight Co., Inc.; #2 Fine Granular
**Includes 60 Gm from Granulating Solution The granulate, G-79, is prepared as described in the general procedure. Potassium bicarbonate, calcium carbonate and sodium bicarbonate are loaded into the blender and are dry mixed for four minutes. A total of 600 Gm of granulating solution is added to the blender while it is running. The blender is run for six minutes after the solution has been added. The granulate is discharged from the mixer and dried.

EXAMPLE 9—Preparation of a Trisodium Citrate and Potassium Bicarbonate Granulate of a Mixture of Acetaminophen, Potassium Bicarbonate, Sodium Bicarbonate and Calcium Carbonate.

| % w/w | Ingredient | Wt. |
|---|---|---|
| | Granulating Solution | |
| 20 | Sodium Citrate, Dihydrate | 400 Gm |
| 10 | Potassium Bicarbonate, U.S.P. | 200 Gm |
| 70 | D.I. Water | 1400 Gm |
| 100 | | 2000 Gm |
| | Granulate, G-81 | |
| 27.6 | Acetaminophen, U.S.P. | 1100 Gm |
| 21.0 | Potassium Bicarbonate, U.S.P. | 935 Gm** |
| 26.2 | Sodium Bicarbonate, U.S.P.* | 1100 Gm |
| 22.6 | Precipitated Calcium Carbonate, U.S.P. | 946 Gm |
| 2.6 | Sodium Citrate | 110 Gm |
| 100.0 | | 4191 Gm |

*Church and Dwight Co., Inc.; #2 Fine Granular
**Includes 55 Gm from Granulating Solution The granulate, G-81, is prepared as described in the general procedure. Acetaminophen, potassium bicarbonate, sodium bicarbonate and calcium carbonate are loaded into the blender and are dry mixed for seven minutes. A total of 550 Gm of granulating solution is added to the blender while it is running. The blender is run for six minutes after the solution has been added. The granulate is discharged from the mixer and dried.

G-81 was dry sized through a 0.033 inch opening, drilled S.S. screen at 3550 rpm on a Model JT Homoloid Machine, as it would be for use in a tablet formulation, where material flowability is of importance. A flow test was run by placing 1000 Gm of the sized granulate into a 0.5 inch bottom opening tablet press hopper, set above a recording balance. The granulate was found to flow freely, as required for good manufacturing capability, at approximately 1233 Gm/minute through the hopper opening.

EXAMPLE 10—Preparation of a Tripotassium Citrate Granulate of Sodium Bicarbonate, G-10.

An aqueous solution of tripotassium citrate may also be used as a granulating agent for bicarbonate and will also protect the bicarbonate from reaction with the acid component of a effervescent couple.

| | Granulating Solution | |
|---|---|---|
| % w/w | Ingredient | Wt. |
| 50 | Potassium Citrate, Tribasic | 1000 Gm |
| 50 | D.I. Water | 1000 Gm |
| 100 | | 2000 Gm |

This solution is made by reacting citric acid and potassium bicarbonate as follows:

| Ingredient | Wt. |
|---|---|
| Citric Acid, Anhydrous | 627 Gm |
| Potassium Bicarbonate | 980 Gm |
| D.I. Water | 824 Gm |

The citric acid is dissolved in the water, held in an oversized container. Potassium bicarbonate is added slowly with good mixing while effervescence of the solution proceeds. The effervescent reaction is endothermic so that the solution becomes very cold. The solution is warmed gently back up to about room temperature before it is used.

| | Granulate, G-10 | |
|---|---|---|
| % w/w | Ingredient | Wt. |
| 96.0 | Sodium Bicarbonate, U.S.P.* | 4.8 Kg |
| 4.0 | Potassium Citrate | 0.2 Kg |
| 100.0 | | 5.0 Kg |

*Church and Dwight Co., Inc., #2

The granulate is prepared as described in the general procedure. Sodium bicarbonate is loaded into the blender. It is attrited by running for five minutes with the intensifier bar on. A total of 400 Gm of granulating solution is added to the blender while it is running. The blender is then run for a total of six minutes after the solution addition. The granulate is discharged from the mixer and dried.

The G-10 granulate may be used to prepare an effervescent aspirin tablet formulation.

| | Formula ET-187 | |
|---|---|---|
| mg/tab | Ingredient | Wt. |
| 325 | Aspirin, U.S.P. | 162.5 Gm |
| 1000 | Citric Acid, Anhydrous Powder | 500.0 Gm |
| 2160 | G-10 | 1080.0 Gm |
| 3485 | | 1742.5 Gm |

The G-10 granulate was dry sized by passage through a 2B S.S. drilled screen on a Model M Fitzpatrick Comminuting Mill, operating at 2500 rpm, knives forward. Together the citric acid and aspirin are passed through a #24 S.S. Screen, U.S. Standard. This mixture and the G-10 granulate are loaded into a tabletop Patterson-Kelley Twin Shell Blender, and mixed for seven minutes. The final mixture is compressed into tablets of one inch diameter to a tablet hardness of 9–12 Kp.

The resulting tablets dissolve rapidly (within approximately one minute) when placed in water. The dissolved tablet solution has good esthetic properties; the aspirin crystals on the surface are easily dispersed into the solution by swirling, without leaving an unsightly scum ring on the sides of the glass, and the solution has a prolonged residual effervescence.

EXAMPLE 11

Aspirin containing effervescent tablets made with sodium bicarbonate granulates prepared with different aqueous granulating solutions for comparison. Aqueous solutions of sodium citrate (ET-179, Example 2), potassium citrate (ET-187, Example 10) and dibasic potassium fumarate (ET-339, Example 15) were compared with a similar formulation, made with heat treated sodium bicarbonate, as a control. The tablets were packaged into foil pouches containing two tablets each of the respective formulations, and were tested for stability after 1 week storage at 40° C. Formulations ET-179, ET-187 and ET-339 were used as disclosed and are nonoptimized laboratory formulations. The control is a commercial, optimized product. The tablets were tested for aspirin decomposition, which was followed by the generation of sodium salicylate, and for carbon dioxide generation, which was followed by measurement of the physical expansion of the pouch packages. The following results were obtained:

| | 1 Week 40° C. | |
|---|---|---|
| Formulation | Sodium Salicylate mg/tab | Pouch Expansion mm/pouch |
| ET-179 | 6.35 | 12.7 |
| ET-187 | 5.35 | 3.7 |
| ET-339 | 5.42 | 1.7 |
| Control | 5.50 | 0.9 |

It can be seen from these data that ET-179, ET-187 and ET-339 are approximately equivalent to the control formulation in the matter of sodium salicylate generation as an indicator of aspirin decomposition, but not as resistant to carbon dioxide liberation from the formulations as is the control formulation. However, all three formulations were within acceptable limits, especially for nonoptimized formulations, and were much easier to manufacture since normal wet granulation techniques could be used and special handling was not required.

EXAMPLE 12—Preparation of a Trisodium Citrate Granulate of a Mixture of Acetaminophen and Calcium Carbonate, G-1.

Two particularly troublesome compounds to granulate are acetaminophen and calcium carbonate.

| % w/w | Ingredient | Wt. |
|---|---|---|
| | Granulating Solution | |
| 40.0 | Sodium Citrate, Dihydrate | 600 Gm |
| 60.0 | D.I. Water | 900 Gm |
| 100.0 | | 1500 Gm |
| | Granulate, G-1 | |
| 42.0 | Acetaminophen, U.S.P. | 1772.5 Gm |
| 49.0 | Precipitated Calcium Carbonate, U.S.P. | 2072.5 Gm |
| 9.0 | Sodium Citrate | 380.0 Gm |
| 100.0 | | 4225.0 Gm |

The granulate, G-1, was prepared using the general procedure described previously and used to prepare a swallow tablet.

| | Formula T-48 | |
|---|---|---|
| mg/tab | Ingredient | Wt. |
| 782.82 | G-1 | 626.26 Gm |
| 31.79 | Sodium Starch Glycolate, N.F.* (Explotab) | 25.43 Gm |
| 0.10 | Docusate/Sodium Benzoate (85:15)** | 0.08 Gm |
| 4.00 | Magnesium Stearate, N.F. | 3.20 Gm |
| 10.00 | Crospovidone, N.F. (Polyplasdone XL) | 8.00 Gm |
| 48.29 | Powdered Cellulose, N.F. (Keycel BH65) | 38.63 Gm |
| 9.00 | Colloidal Silicon Dioxide, N.F. (Syloid 244FP) | 7.20 Gm |
| 886.00 | | 708.80 Gm |

*N.F. refers to National Formulary
**Docusate Sodium 85%:sodium benzoate 15% Docusate sodium is the USP name for dioctyl sodium sulfosuccinate The G-1 granulate was dry sized by passage through a 0.033 inch opening, drilled S.S. screen at 3550 rpm, on a Model JT Homoloid Machine from the W. J. Fitzpatrick Co. All ingredients except the magnesium stearate were passed through a #24 U.S. Standard S.S. screen two times, and then mixed in a two quart capacity V-Blender for five minutes. The magnesium stearate was delumped by spatulation and then added to the V-Blender, and the whole composition was mixed for three minutes. The composition was compressed into tablets using 0.300"×0.700"×0.050" (cup depth) capsule shaped tooling on a Colton 216 tablet press.

The resulting tablets had a cross sectional breaking strength of 4.6 Kp, and showed U.S.P. dissolution test results of 94.0% at 30 minutes for acetaminophen and 99.9% at 30 minutes for calcium.

EXAMPLE 13—Preparation of a Dipotassium Fumarate Granulate of Potassium Bicarbonate, G-83.

| % w/w | Granulating Solution Ingredient | Wt. |
|---|---|---|
| 19.2 | Potassium Fumarate, Dibasic | 1000 Gm |
| 80.8 | D.I. Water | 4200 Gm |
| 100.0 | | 5200 Gm |

This solution is made by reacting fumaric acid and potassium bicarbonate as follows:

| Ingredient | Wt. |
|---|---|
| Fumaric Acid, N.F. | 601 Gm |
| Potassium Bicarbonate, U.S.P. | 1036 Gm |
| D.I. Water | 4014 Gm |

The potassium bicarbonate was dissolved in the water, the fumaric acid added slowly with mixing while effervescence of the solution proceeds. The solution is warmed gently to about 44° C. before it is used.

| % w/w | Granulate G-83 Ingredient | Wt. |
|---|---|---|
| 97.4 | Potassium Bicarbonate, U.S.P. | 5000 Gm |
| 2.6 | Potassium Fumarate, Dibasic | 135 Gm |
| 100.0 | | 5135 Gm |

The G-83 granulate was prepared as described in the general procedure outlined previously.

EXAMPLE 14—Preparation of a Potassium Sodium Tartrate Granulate of Potassium Bicarbonate, G-85.

| % w/w | Ingredient | Wt. |
|---|---|---|
| | Granulating Solution | |
| 40.0 | Potassium Sodium Tartrate, U.S.P. | 500 Gm |
| 60.0 | D.I. Water | 750 Gm |
| 100.0 | | 1250 Gm |
| | Granulate, G-85 | |
| 94.7 | Potassium Bicarbonate, U.S.P. | 5000 Gm |
| 5.3 | Potassium Sodium Tartrate, U.S.P. | 280 Gm |
| 100.0 | | 5280 Gm |

The G-85 granulate was prepared as described in the general procedure outlined previously.

Test of dry state reactivity of micronized fumaric acid with dipotassium fumarate granulate of potassium bicarbonate, G-83, and with potassium sodium tartrate granulate of potassium bicarbonate, G-85.

Testing was conducted according to Example 1. There was no perceptible reaction of G-83 or G-85 with micronized fumaric acid over 45 hours.

EXAMPLE 15—Preparation of a Dipotassium Fumarate Granulate of Sodium Bicarbonate, G-84.

The granulating solution of dipotassium fumarate described in Example 13 was used to prepare granulate G-84. The granulate was prepared as described in the general procedure outline previously.

| % w/w | Granulate G-84 Ingredient | Wt. |
|---|---|---|
| 97.75 | Sodium Bicarbonate, U.S.P.* | 5000 Gm |
| 2.25 | Potassium Fumarate, Dibasic | 115 Gm |
| 100.00 | | 5115 Gm |

The G-84 granulate was used to prepare an effervescent aspirin tablet formulation.

| mg/tab | Formula ET-339 Ingredient | Wt. |
|---|---|---|
| 1983 | G-84 | 594.9 |
| 1000 | Citric Acid, Anhydrous Powder | 300.0 |
| 324 | Aspirin, U.S.P. | 97.2 |
| 3307 | | 992.1 |

The procedure used to test the tablets has been outlined in Example 10. The results were generally the same as those shown in Example 10. A comparison of effervescent tablets made with this method is shown in Example 11.

EXAMPLE 16

Spray Dried Granulation Example

Granulates of this invention may be prepared by various pharmaceutical technologies of granulators, according to the needs of the desired end product. Accordingly, fluid bed granulators, roller compactors, vacuum granulators, spray driers and the like may also be used to prepare granulates according to this invention. To illustrate this practice, a trisodium citrate granulate of a mixture of calcium carbonate, potassium bicarbonate and sodium bicarbonate was prepared as follows:

| % w/w | Spray Drying Solution and Slurry, for SD-2 Ingredient | Weight |
|---|---|---|
| 19.6 | Potassium Bicarbonate, U.S.P. | 1432 Gm. |
| 18.2 | Precipitated Calcium Carbonate, U.S.P. | 1336 Gm. |
| 19.6 | Sodium Bicarbonate, U.S.P.* | 1432 Gm. |
| 12.6 | Sodium Citrate, Dihydrate | 922 Gm. |
| 30.0 | D.I. Water | 2195 Gm. |
| 100.0 | | 7317 Gm. |

*Church and Dwight Co., Inc., #2

The solution and slurry is prepared by dissolving the sodium citrate in the D.I. Water with stirring, using a laboratory mixer at high speed. The calcium carbonate is added and mixed in, and then the potassium bicarbonate and sodium bicarbonate are added with high speed mixing. Mixing is stopped, and the whole slurry is sheared for two minutes using a Gifford-Wood Bench Top Homogenizer. Shearing is stopped and the slurry is ready for spray drying, during which time slow mixing is used to keep the slurry from sedementing.

A Bowen No. 1 Tower spray drier, equipped with a Type 59 SC two-fluid nozzle assembly was used to spray dry the slurry. A Netzsch Nemo 4NL20A Pump was used to deliver the slurry to the spray drier. 80 p.s.i.g. of air pressure was delivered to the 59 SC nozzle. The slurry was fed to the drier at 100 Gm./min. The inlet air temperature was held between 470° and 500° F., and the outlet temperature between 302° and 306° F. The collected granulation had the following calculated composition on a dried basis:

| SD-2 | |
|---|---|
| % w/w | Ingredient |
| 28.0 | Potassium Bicarbonate, U.S.P. |
| 26.0 | Precipitated Calcium Carbonate, U.S.P. |
| 28.0 | Sodium Bicarbonate, U.S.P. |
| 18.0 | Sodium Citrate, Dihydrate |
| 100.0 | |

The SD-2 granulate was used to prepare an effervescent aspirin tablet formulation.

| Formula ET-1 | | |
|---|---|---|
| Mg/Tab | Ingredient | Weight |
| 1072 | SD-2 | 321.6 Gm. |
| 325 | Aspirin, U.S.P. | 97.5 Gm. |
| 1000 | Citric Acid, Anhydrous Powder | 300.0 Gm. |
| 39 | Aspartame Granulation* | 11.7 Gm. |
| 559 | DiPac, Sugar | 167.7 Gm. |
| 5 | Polyvinylpyrrolidone, K-90 | 1.5 Gm. |
| 3000 | | 900.0 Gm. |

*Aspartame Granulation according to U.S. Pat. No. 4,783,331 comprised of Aspartame 20.44% w/w, Nonionic Surfactant 0.95% w/w, and Lactose 78.60% w/w.

All ingredients except SD-2 were passed thru a #24 mesh screen. These, plus the SD-2, were added to a 2 L. container and mixed for 7 minutes on a Turbula T10B Mixer at 14 RPM. Tablets were compressed using one inch round, flat-face, beveled edge tooling, on a kilian RT116 tablet press, and packaged into twin-pak foil pouches.

Effervescent tablet formulations of buffered aspirin medicament are noted for their physical and chemical instability. ET-1 represents a significant advance in the technology of such formulations. Hence, evidence of this superior stability is presented below.

A formulation that is similar in basic structure to ET-1 (presented below) is useful as a guide to illustrate the significant improvement in physical and chemical stability represented by ET-1.

| Comparative Formulation (C.F.) | |
|---|---|
| Mg/Tab | Ingredient |
| 325 | Aspirin, U.S.P. |
| 300 | Precipitated Calcium Carbonate, U.S.P., 83% Granulation* |
| 300 | Potassium Bicarbonate, U.S.P., (dried) |
| 345 | Sodium Bicarbonate, U.S.P., 86% Heat Treated |
| 400 | Glycine, U.S.P. |
| 770 | Citric Acid, Anhydrous Powder |
| 500 | DiPac ® Sugar |
| 25 | Phenylopropanolamine Bitartrate |
| 2 | Chlorpheniramine Maleate, U.S.P. |
| 2967 | |

*Calcium Carbonate granulation according to U.S. Pat. No. 4,783,331; see Table III, columns 7 and 8.

Formulation ET-1 was tested for aspirin decomposition by chemical assay, reported as sodium salicylate content, and for physical stability by measurement of foil pouch expansion.

| ET-1 | | | |
|---|---|---|---|
| | 8 Weeks | | |
| | RT | 40° C. | 50° C. |
| Sodium Salicylate Mg/tab | 2.94 | 9.60* | 21.1 |
| | 5-Days | | |
| | RT | 40° C. | |
| Pouch Expansion Mm/pouch | zero | zero | |

*52 day value instead of 56 day value.

Formulation C.F. was likewise tested for aspirin decomposition by sodium salicylate assay and for physical stability by pouch expansion testing.

| C.F. | | | | |
|---|---|---|---|---|
| | Initial | 2 wks 40° C. | 4 wks 40° C. | 8 wks 40° C. |
| Sodium Salicylate Mg/tab | 1.44 | 5.22 | 8.56 | 50.4 |
| | 1 wk 40° C. | 2 wks 40° C. | 4 wks 40° C. | 8 wks 40° C. |
| Pouch Expansion Mm/pouch | 0.7 | 1.9 | 7.7 | >12.5* |

*Value exceeded the limits of the measuring device.

It is readily apparent from the stability test data, that ET-1 represents a significant improvement over the stability of formulation C.F. which is a formulation of standard preexisting technology.

It should be understood that many modifications and variations can be made in the proportions and components used herein without departing from the spirit and scope of the invention, which is solely defined by the claims.

What is claimed is:

1. A method of granulating a finely divided solid material, comprising the steps of:
   a. preparing an aqueous granulating solution by dissolving an alkali metal salt of an edible organic acid selected from the group consisting of trisodium citrate, tripotassium citrate, dipotassium fumarate and sodium potassium tartrate in water;
   b. mixing an amount of the aqueous granulating solution effective to produce a moist mass on mixing with a finely divided solid material requiring granulation, the solid material selected from the group consisting of potassium bicarbonate, acetaminophen, calcium carbonate, sodium bicarbonate, ketoprofen and a combination thereof; and
   c. granulating and drying the mixture.

2. A granulation mixture composed of:
   a. an aqueous solution of a bicarbonate chosen from sodium or potassium bicarbonate and an alkali metal salt selected from the group consisting of trisodium citrate, tripotassium citrate, dipotassium fumarate and sodium potassium tartrate which aqueous solution is present in an amount effective to produce a moist mass on mixing; and
   b. a finely divided solid chosen from the group consisting of potassium bicarbonate, acetaminophen, calcium carbonate, sodium bicarbonate, ketoprofen or a combination thereof.

3. A method of preparing an effervescent tablet formulation, comprising the steps of:

a. preparing an aqueous granulating solution by dissolving an alkali metal salt of an edible organic acid selected from the group consisting of trisodium citrate, tripotassium citrate, dipotassium fumarate and sodium potassium tartrate in water;
b. mixing the aqueous granulating solution in an amount effective to produce a moist mass on mixing with a finely divided solid material requiring granulation, the solid material selected from the group consisting of potassium bicarbonate, acetaminophen, calcium carbonate, sodium bicarbonate, ketoprofen and a combination thereof;
c. granulating and drying the mixture; and
d. forming an effervescent tablet.

4. A method of granulating a finely divided solid material comprising the steps of:
a. preparing an aqueous granulating solution by dissolving a sodium or potassium or a mixed sodium or potassium salt of an edible organic acid chosen from the group consisting of citric acid, fumaric acid, tartaric acid and malic acid;
b. mixing an amount of the aqueous granulating solution effective to produce a moist mass on mixing with a nonacid or slightly acidic, finely divided, medically effective solid ingredient requiring granulation;
c. granulating and drying the mixture.

* * * * *